United States Patent [19]

Chirila et al.

[11] Patent Number: 5,458,819
[45] Date of Patent: Oct. 17, 1995

[54] METHOD OF PRODUCING A KERATOPROSTHESIS

[75] Inventors: Traian V. Chirila, Hillarys; Ian J. Constable, Mosman Park; Geoffrey J. Crawford, Floreat Park; Albert V. Russo, Yokine, all of Australia

[73] Assignee: Lions Eye Institute of Western Australia, Incorporated, Australia

[21] Appl. No.: 170,379

[22] Filed: Dec. 20, 1993

Related U.S. Application Data

[62] Division of Ser. No. 931,027, Aug. 14, 1992, Pat. No. 5,300,116.

[30] Foreign Application Priority Data

Aug. 5, 1992 [AU]  Australia ................. 20824/92

[51] Int. Cl.⁶ ..................................... B29D 11/00
[52] U.S. Cl. ................. 264/1.7; 264/2.4; 264/2.7; 264/28; 425/808
[58] Field of Search .................. 264/1.7, 1.9, 2.4, 264/2.7, 28; 623/5, 6; 425/808

[56] References Cited

U.S. PATENT DOCUMENTS

| | | |
|---|---|---|
| 4,021,382 | 5/1977 | Stoy et al. . |
| 4,093,361 | 6/1978 | Erickson et al. ............... 623/6 |
| 4,588,406 | 5/1986 | Fedorov et al. ............... 623/6 |
| 4,865,601 | 9/1989 | Caldwell et al. ............... 623/5 |
| 4,932,968 | 6/1990 | Caldwell et al. . |
| 4,936,850 | 6/1990 | Barrett . |
| 5,002,568 | 3/1991 | Katzen . |
| 5,032,131 | 7/1991 | Aysta et al. . |
| 5,108,428 | 4/1992 | Capecchi et al. . |
| 5,246,634 | 9/1993 | Ichikawa et al. ............... 264/1.7 |

FOREIGN PATENT DOCUMENTS

| | | |
|---|---|---|
| 2649605 | 7/1989 | France . |
| 63-191606 | 8/1988 | Japan ............... 623/6 |
| 1380743 | 3/1988 | U.S.S.R. . |
| 2215076 | 9/1989 | United Kingdom ............... 623/6 |
| WO93/13731 | 7/1993 | WIPO ............... 623/6 |

OTHER PUBLICATIONS

Leagais, J–M., et al., "Keratoprosthesis: A comparative study of three different microporous polymer and first application in human eyes", *Investigative Ophthalmology & Visual Science*, 32:778 (1991).

Hwang, W–J., et al., "Clinico–Pathologic Study of Gore–Tex Patch Graft in Corneoscleral Surgery", *Investigative Ophthalmology & Visual Science*, 33:992 (1992).

Trinkaus–Randall, V., et al., "In Vitro Evaluation of Fibroplasia in a Porous Polymer", *Investigative Ophthalmology & Visual Science*, 31(7):1321–1326 (1990).

Trinkaus–Randall, V., et al., "Development of a Biopolymeric Keratoprosthetic Material—Evaluation In Vitro and In Vivo", *Investigative Ophthalmology & Visual Science*, 29(3):393–400 (1988).

Jacob–LaBarre, J. T., et al., "Development of a New Type of Artificial Cornea for Treatment of Endstage Corneal Diseases", *Progress in Biomedical Polymers*, pp. 27–39 (1990).

*Primary Examiner*—Mathieu D. Vargot
*Attorney, Agent, or Firm*—Walter H. Dreger

[57] ABSTRACT

A composite device which may be implanted in the cornea of the human eye to replace damaged or diseased portions, and a method of manufacturing the said device, are disclosed. The device consists of a transparent central portion intimately attached to an opaque spongy rim. Both portions are made of hydrogel materials produced in different conditions of polymerization during a two-stage process performed in a specific moulding unit. The spongy rim promotes and maintains cellular invasion from the host corneal tissue, thus providing a tight union between implant and recipient cornea which prevents the postoperative extrusion of the implant.

28 Claims, 5 Drawing Sheets

METHOD OF PRODUCING A KERATOPROSTHESIS

This is a division of application Ser. No. 07/931,027 filed 14 Aug. 1992, now U.S. Pat. No. 5,300,116.

FIELD OF THE INVENTION

This invention relates to a composite prosthetic corneal device that after implantation is substantially incorporated into the host tissue by cellular invasion along the circular peripheral zone which is made essentially of a polymeric hydrophilic sponge surrounding the central optic zone made of a transparent hydrophilic polymer.

BACKGROUND OF THE INVENTION

The cornea is not only a major component of the optical system of the human eye, by providing about 75% of the total dioptric power, but also serves a protective function against a possible hostile environment. In order to perform normally its functions (refraction, transmission, protection), the cornea must actively maintain its transparency and integrity throughout life.

Replacement of an injured and/or opaque cornea with artificial materials has a long history of failure and even today its success is very limited.

As an alternative, the transplantation of human homologous corneal tissue is successful in less complex pathological conditions, such as keratocomus or corneal dystrophies. However, with gross scarring of the cornea, particularly when the host tissue is deeply vascularized, the tear film characteristics are altered, or secondary glaucoma is present, as may occur in conditions such as alkali burns, ocular pemphigoid, Stevens-Johnson syndrome, trachoma and other conditions, the clear graft rate drops significantly. Graft rejection or late graft failure decrease furthermore the chances of a successful transplantation. In addition, even in the countries with organized eye banking systems, there is a chronic shortage of donor corneal tissue. In the developing countries, less than 1% of the required transplants are carried out due to lack of availability of tissue and technology. If an artificial cornea (keratoprosthesis) was available with relatively simple means of fixation then millions more people worldwide might obtain visual rehabilitation.

The material almost exclusively used for keratoprostheses has been poly(methyl methacrylate), henceforth designated as PMMA. Despite a long recorded history, the success of various types of keratoprosthesis made from PMMA is still limited, mainly because of complications due to lack of healing at the interface between stromal tissue and peripheral prosthetic material, such as erosive tissue necrosis (melting), leakage of aqueous humor, epithelialization, infection, and extrusion of the implant.

Poly(2-hydroxyethyl methacrylate) hydrogel, henceforth designated as PHEMA, was another prosthetic material which received interest from ophthalmologists. Biocompatibility of PHEMA in the cornea is now well established, having been used as implant material for keratophakia (intracorneal lenses), as well as for epikeratoplasty. To a lesser extent, PHEMA has also been proposed as a material for keratoprostheses, showing good results in the animal models.

For many years, attempts have been made to use polymers such as PMMA, PHEMA, or other materials for keratoprosthetic implants. These attempts are well documented by the patent literature, for example in U.S. Pat. Nos. 2,517,523; 2,714,721; 2,754,520; 2,952,023; 3,454,966; 3,458,870; 3,945,054; 4,346,482; 4,402,579; 4,470,159; 4,586,929; 4,612,012; 4,624,669; 4,676,790; 4,693,715; 4,772,283; and 5,030,230, and in Ger. Pat. No. 2705234; Neth. Pat. No. 8501403; and Fr. Pat. No. 2,649,605. For general reviews covering the modern history of keratoprosthesis see: Day, R., Transactions of the American Ophthalmological Society, vol. 55, pp. 455–475 (1957), "Artificial corneal implants"; Stone Jr., W., Yasuda, H. and Refojo, M. F., "A 15-year study of the plastic artificial cornea-basic principles", in *The Cornea World Congress*, King Jr., J. H. and McTigue, J. W., eds., Butterworths, Washington, 1965, pp. 654–671; Polack, F. M., British Journal of Ophthalmology, vol. 55, pp. 838–843 (1971), "Corneal optical prostheses"; Mannis, M. J. and Krachmer, J. H., Survey of Ophthalmology, vol. 25, pp. 333–338 (1981), "Keratoplasty: A Historical Perspective"; Barron, B. A., "Prostokeratoplasty", in *The Cornea*, Kaufman, H. E., McDonald, M. B., Barron, B. A. and Waltman, S. R., eds., Churchill Livingstone, New York, 1988, pp. 787–803.

The postoperative complications of PMMA implants appear to be caused by the lack of a firm bond between the remaining corneal tissue and these implants. Prostheses have therefore been designed consisting of two distinct parts, namely a central optic cylindrical zone (PMMA), and a surrounding skirt made of materials different from PMMA such as metals, ceramics, preserved biological tissue and various polymers. However, all these modifications did not lower significantly the implant extrusion rate, as revealed in the above mentioned reviews. It therefore became clear that biocompatibility alone is not sufficient to overcome the problems of melting, leakage and extrusion. Ideally, the peripheral material should be incorporated into the host biological substrate by cellular invasion and growth across the interlace between material and tissue.

PRIOR ART

Based upon the concept of a firm biological bonding between the peripheral prosthetic material and corneal tissue, some suggestions to use porous materials have been recently disclosed.

In two publications by Trinkaus-Randall et al., in Investigative Ophthalmology and Visual Science, vol. 29, pp. 393–400 (1988) and vol. 31, pp. 1321–1326 (1990), the suggestion to use a composite keratoprosthesis is disclosed. The central optic zone is made of a hydrophilic poly(vinyl alcohol) copolymer, and the skirt is made of a hydrophobic fibrous melt-blown web prepared from a blend of polybutylene and polypropylene. Both materials are manufactured by 3M Company, St. Paul, Minn., U.S.A. Whilst in vitro tests have shown cellular invasion into the fibrous web, there is no proof that the two materials can be joined together as a keratoprosthetic device since their interfaces have very different chemical and physical properties.

In a publication by Jacob-LaBarre and Caldwell, in *Progress in Biomedical Polymers*, Plenum Press, New York, 1990, pp. 27–39, a composite keratoprosthesis is disclosed which consists of a central optic zone made of a hydrophilic polyurethane, and a skirt with a long six-prong haptic made of porous polytetrafluoroethylene (Gore-Tex®, W. L. Gore &. Associates, Inc., Flagstaff, Ariz., U.S.A.). This keratoprosthesis is designated for a deep anchoring into the sclera. A good performance one year after implantation in animals is disclosed. However, the fabrication of the device is difficult, involving casting of polyurethane into the central hole of porous polytetrafluoroethylene, followed by heat treatment under pressure in order to create a proper curvature of the optic zone, and finally hydration. Both heat-pressure treatment and hydration may cause distortion of the junction between the hydrophilic centre and hydrophobic periphery. No particular details of the technique are disclosed.

A keratoprosthesis constituted of a skirt made of porous polytetrafluoroethylene, henceforth designated as PTFE, is also disclosed by Legeais et al. in Fr. Pat. No. 2,649,605 and in Investigative Ophthalmology and Visual Science, vol. 32 (Suppl.), p. 778 (1991). The central optic zone is made of PMMA and comprises a ring with indented interior surface, and a lens. The lens is fastened into the ring through the grooves of the ring. Both transparent elements have peripheral collars positioned against each other in a jaw-like manner. The porous PTFE ring is entrapped between PMMA ring and lens, and gripped between their peripheral collars. This keratoprosthesis has a number of drawbacks. It is too complicated to manufacture, and the design as proposed appears unlikely to assure a proper joining of the porous PTFE to the PMMA ring. Also, it is not yet known whether porous PTFE is an ideal material for the corneal tissue invasion. Negative results with these materials in the cornea have been reported by Hwang and Hu in Investigative Ophthalmology and Visual Science, vol. 33 (Suppl.), p. 992 (1992).

SUMMARY OF THE INVENTION

Accordingly, it is the prime object of this invention to provide a one-piece composite keratoprosthesis which comprises a central transparent portion made of a biocompatible hydrophilic polymer, henceforth designated as hydrogel, and a peripheral portion made of a biocompatible hydrophilic polymeric sponge, henceforth designated as hydrogel sponge, the said portions being intimately attached. The central hydrogel and the hydrogel sponge are made of polymers similar in composition, both essentially based on the monomer 2-hydroxyethyl methacrylate, henceforth designated as HEMA.

It is another object of this invention to provide a method for the production of the said composite device, including the design of a moulding unit in which the said device can be made by a sequential polymerization of HEMA.

Another object of this invention is to provide a keratoprosthesis which can be implanted using only simple surgical techniques.

Yet another object of this invention is to provide a keratoprosthesis which is easy to manufacture, therefore available in abundant supply.

Briefly stated, the keratoprosthesis of the present invention comprises first a peripheral circular portion as the rim of the device, made by homopolymerization or copolymerization in solution of HEMA using large excess of water and resulting in a nontransparent hydrogel sponge. In the central aperture of the said sponge, a transparent circular portion is created by the subsequent polymerization or copolymerization in solution of HEMA using lower amounts of water than in the case of the sponge formation. Alternatively, the central portion can be firstly created, and followed by the production of the spongy rim in the manner disclosed above. Regardless of the succession of the two processes, through this sequential two-stage polymerization performed in the same mould, a tight and intimate attachment between the materials in the two portions of keratoprosthesis is achieved due to the fact that, during the second stage, the monomer mixture firstly penetrates to some extent into the pre-existent polymer matrix and only afterwards undergoes polymerization. As a result, an interpenetrating polymer network (IPN) region is formed along the boundary between the central portion and rim.

A requirement of the present invention is that the low molecular weight residuals, such as unreacted monomers, initiators, and crosslinking agents, have to be removed from the finished keratoprosthesis prior to its use. Their removal is performed by static extraction in water for at least one week, with frequent water exchanges, until a steady state is reached in which the rate of extraction is very low, preferably zero, and constant. Another requirement of the present invention is that the water-extracted keratoprosthesis must be sterilized prior to its use by the methods commonly employed in the art. Prior to implantation, the keratoprosthesis of the present invention can be impregnated with collagen, or can be used as such.

Applicants' experiments have shown that PHEMA hydrogel sponges allow the invasion of cells from the host corneal stroma into the pores of the sponge.

In view of the foregoing discussion, this invention will be more fully described by consideration of the preferred embodiment.

BRIEF DESCRIPTION OF THE DRAWINGS

The invention will also be illustrated in conjunction with the accompanying drawings in which.

DESCRIPTION OF THE PREFERRED EMBODIMENT

Figure 1:
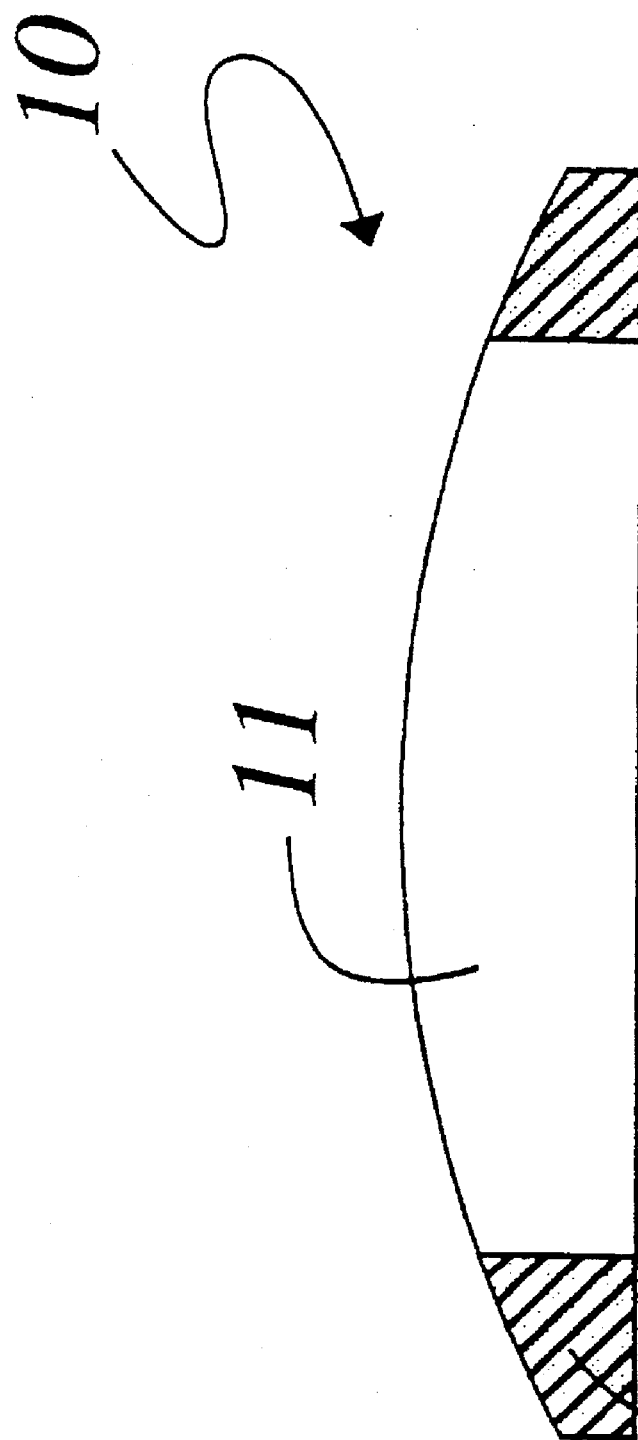
FIG. 1 is a cross-sectional view of a keratoprosthesis of the invention, with a flat posterior surface.
Figure 2:
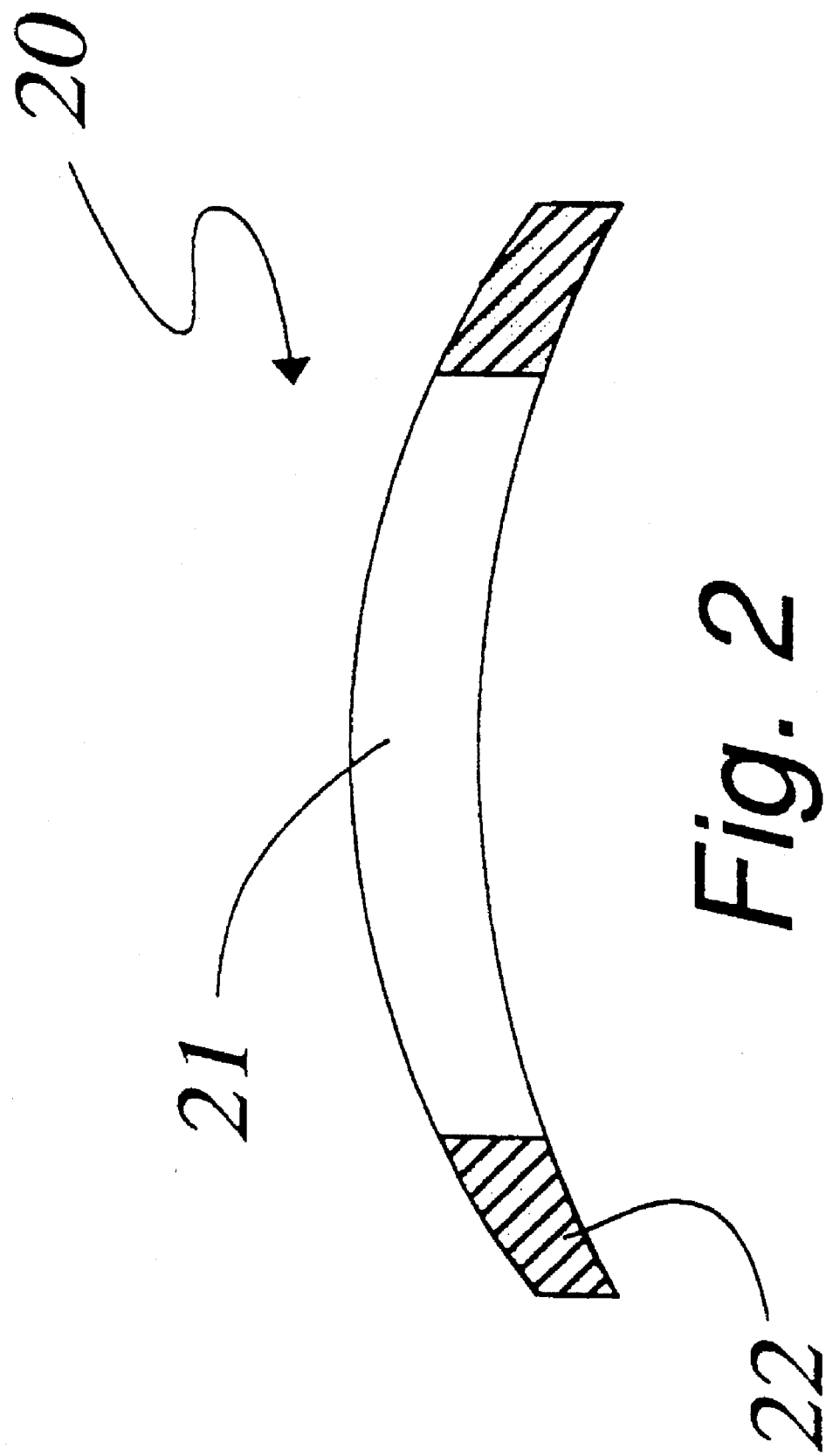
FIG. 2 is a cross-sectional view of a keratoprosthesis of the invention, with a curved posterior surface.

With reference to FIG. 1, a device of the invention is shown generally as 10 and includes a central transparent portion 11 and a peripheral portion typified by a circular rim 12. The posterior surface of the device may be flat as shown in FIG. 1, or it may have any required radius of curvature as depicted in FIG. 2 in which the keratoprosthesis 20 comprises a central portion 21 and a rim 22. The desirable thickness of the rim 12 or 22 is approximately the same as the thickness of the host cornea tissue into which it is to be implanted. The thickness is such that the rim should withstand the forces exerted during implantation with no tearing or permanent deformation.

Figure 3:
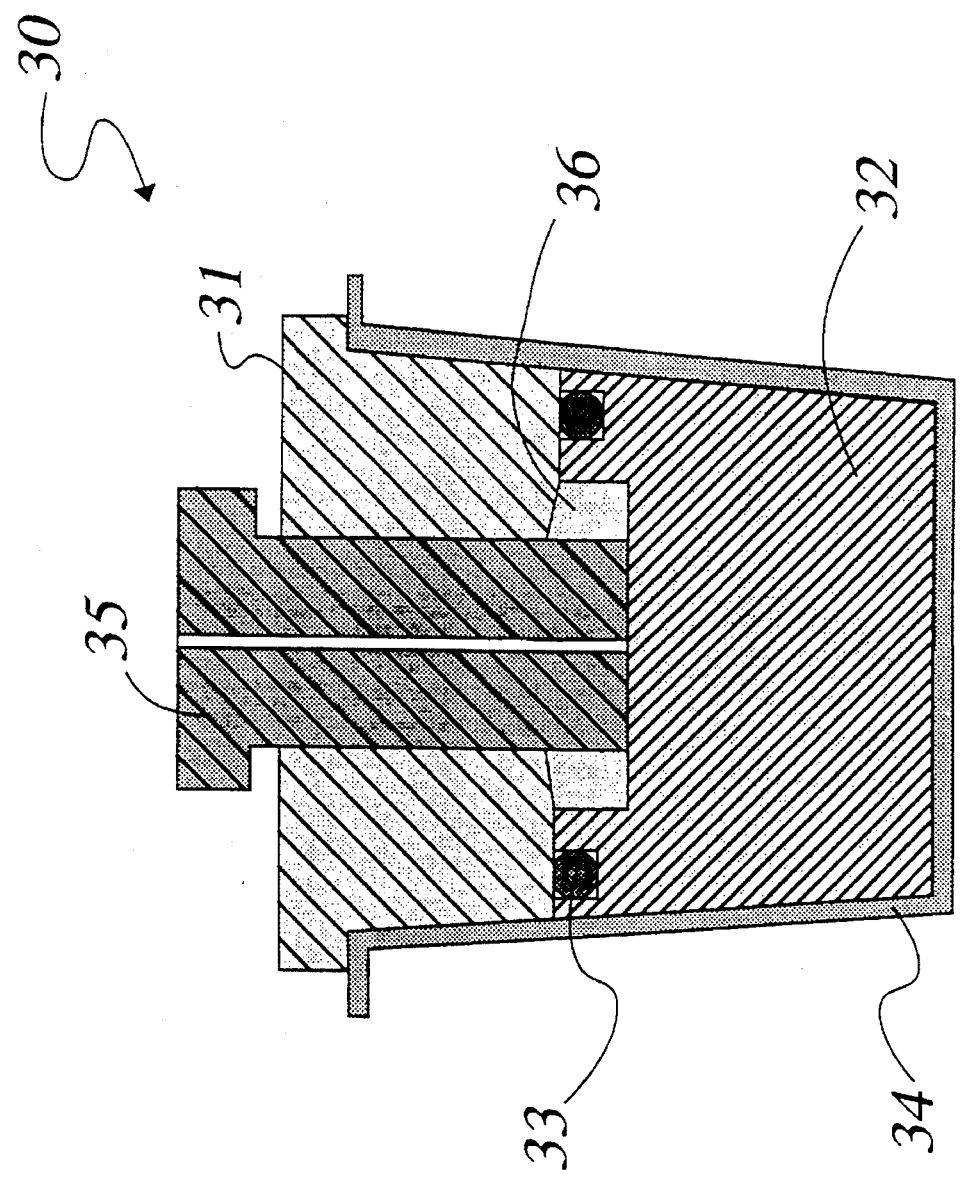
FIG. 3 is a cross-sectional view of the moulding system for making the prosthetic rim, in the first stage of the manufacture of a keratoprosthesis of the invention.
Figure 4:
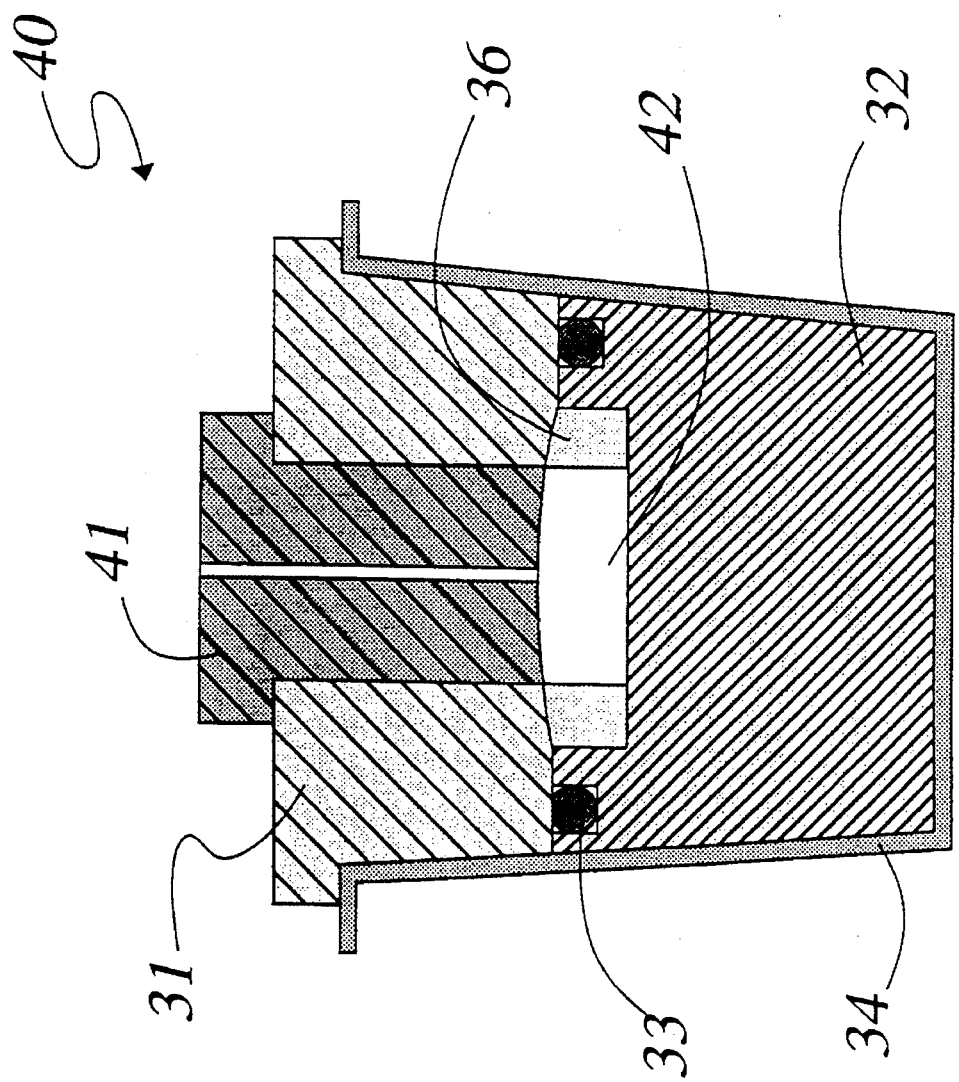
FIG. 4 is a cross-sectional view of the moulding system for making the central portion of the prosthesis, in the second and final stage of the manufacture of a keratoprosthesis of the invention.

FIGS. 3 and 4 depict the moulding system and the two stages of making the device of the invention. Each stage comprises a polymerization in water of HEMA as such or mixed with other comonomers, in presence of crosslinking agents and initiators.

The cylindrical mould to be used in the first stage, that is the manufacture of the rim, is shown in FIG. 3, generally as 30, and consists of an annular head 31, a base 32, both made preferably of Teflon®, an O-ring seal 33, made of Viton®, and a housing 34, made of polypropylene. The liquid monomeric mixture for the production of the spongy rim is introduced by means of a syringe into the empty space 36, in large excess. The space 36 is created by assembling and clamping together the head 31 and base 32, sealed through the O-ring 33, within the housing 34. Any suitable clamping device may be used without constituting a part of this invention. The assembled system, including the monomeric mixture, is subjected to a moderate vacuum at room temperature for 5 minutes in order to eliminate possible air bubbles in the liquid mixture 36. The plunger 35, having a cylindrical hole bored through its centre, is then inserted slowly through the central hole in the head 31 and pushed carefully further until it touches the base 32. During this operation, the excess of monomeric mixture is forced out through the hole in the plunger 35. The moulding system, including the monomeric mixture 36 and the plunger 35, is then maintained at a temperature between 50° and 80° C. in an oven, for 5 to 10 hours. During this time, the polymerization of the monomeric mixture takes place in 36.

The monomeric mixture is essentially an aqueous solution of a hydrophilic monomer, preferably HEMA or its mixture with hydrophilic or hydrophobic monomers, of 5 to 25% by weight concentration in water. To this solution, a crosslinking agent (0.2 to 1% by weight based on the total amount of monomers), and a water-soluble initiator (0.05 to 1% by weight based on the total amount of monomers) are added.

Representative of other monomers useful in conjunction with HEMA as comonomers of the present invention are:

a. Other hydroxylated methacrylates and acrylates, such as 2-hydroxyethyl acrylate, 2-hydroxypropyl methacrylate and acrylate, glycerol methacrylates and acrylates, and many others well known in the art, as such or mixtures thereof.

b. Acrylamide derivatives and N-vinylpyrrolidone, and various combinations thereof.

c. Hydrophobic methacrylates and acrylates, such as methyl methacrylate or other members of the aliphatic homologue series, and 2-alkoxyethyl methacrylates and acrylates.

d. Other hydrophobic monomers, such as vinyl acetate and vinyl propionate.

Whilst the hydrophilic monomers may be added to HEMA in any proportion from 1 to 50% by weight based on the total amount of monomers, the hydrophobic monomers may be added in a proportion not higher than 5%, in order to avoid the occurrence of phase separation prior to polymerization.

As crosslinking agents, any polyfunctional methacrylate or acrylate, bis(acrylamides), or divinyl derivatives, all well known in the art, may be used.

As initiators for the polymerization process, water-soluble agents are preferred, either inorganic, such as aqueous solutions of sodium metabisulfite and ammonium persulfate added in succession, or organic agents, such as 2,2'-azo-bis(N,N'-dimethyleneisobutyramidine)dihydrochloride or 2,2'-azobis(2-amidinopropane)dihydrochloride, both supplied by Wako Pure Chemical Industries Ltd., Osaka, Japan, as V-044® and V-50®, respectively.

In a preferred formulation for the production of the prosthetic rim of the invention, 2 g HEMA are mixed with 0.01 g ethylene dimethacrylate as a crosslinking agent. To this mixture, 8 g distilled water are added and the resulting solution (20% by weight HEMA in water) is thoroughly homogenized in a laboratory shaker. Following this, 20 microliters of a solution 12% by weight sodium metabisulfite in water are added as the first component of the initiating system, and the mixture is homogenized for 5 minutes in an ultrasonic bath. Before placing the mixture into the mould, 20 microliters of a solution 12% by weight ammonium persulfate in water are added as the second initiating component, and this final mixture is rapidly homogenized by vigorous shaking, then immediately loaded in a syringe, and then slowly injected into the empty enclosure 36 of the mould 30. The polymerization is then performed in the mould as aforedescribed, at 50° C. for 6 hours.

To understand better the process of formation of the hydrophilic sponges constituting the rim of the keratoprosthesis, the following considerations are made, which do not constitute per se a part of this invention. PHEMA hydrogels are essentially porous materials. Different porosities result from different polymerization techniques. Depending on their average pore size, there are two main categories of hydrogels. By the bulk polymerization technique of HEMA, a glassy and transparent polymer is produced which swells in water and becomes soft and flexible. Although it allows the transfer of swelling agents and of some small molecules, this kind of PHEMA is considered "nonporous". The spaces between macromolecular chains are the only available loci for the mass transfer, which suggests that the pore size is within the range of molecular dimensions, namely several nanometers. When PHEMA is obtained by polymerization in solution, by increasing the amount of diluent in the monomeric mixture, the pore size will also increase, so that "microporous" (10 to 100 nanometers) and "macroporous" (100 nanometers to 1 micrometer) hydrogels can be produced. These hydrogels are still transparent like the "nonporous" ones. They are all known as homogeneous hydrogels and represent a distinctive class of PHEMA hydrogels for which the generic term of "gels" is used. However, when a nonsolvent for PHEMA is used as a diluent in the monomeric mixture, in amounts exceeding the maximum swelling capacity of the final polymer in that particular diluent, phase separation occurs resulting in heterogeneous hydrogels which are milky to white materials. The most commonly used diluent is water, which is an excellent solvent for HEMA but a nonsolvent for PHEMA, even when the latter is not crosslinked. By using a concentration of water in the initial monomeric mixture higher than a critical value, which for PHEMA is around 45% by weight, heterogeneous hydrogels are produced. With a porosity much higher (5 to 80 micrometers) than that of the homogeneous hydrogels, they are true "sponges". The formation of PHEMA sponges in a large excess of water is a result of the dramatic decrease of the solubility of HEMA as the polymerization proceeds. The monomer phase, already enriched in polymer, gradually separates as droplets which join together. By the end of the polymerization process, the polymer droplets have become fixed in a network populated by large voids, sometimes interconnected, occupied by the water phase that had also separated in the meantime.

The cylindrical mould to be used in the second stage of the manufacturing of keratoprosthesis according to this invention, that is the production of the central portion, is shown in FIG. 4, generally as 40, and consists of a head 31, a base 32, an O-ring 33, and a housing 34. This mould is the same as the one used in the previous stage and depicted in FIG. 3, except for a different plunger henceforth designated as 41. Following the removal of the plunger 35 at the end of the previous stage, a space 42 is left empty and surrounded by the spongy rim 36 which was constructed during the first stage of the manufacturing process. If necessary, the enclosure 42 may be cleaned of debris prior to its loading with monomeric mixture. The liquid monomeric composition for the production of the transparent central portion is then slowly added by using a syringe into the space 42 of the unit 40, assembled and clamped, preferably dropwise in order to avoid the formation of air bubbles. The plunger 41, of a precise length, provided with a cylindrical hole along its vertical axis and a shoulder at the top end, is slowly inserted through the central hole of the head 31, and pushed carefully until its shoulder stops at the top surface of the head 31. The excess of monomeric mixture is forced out through the hole in the plunger 41. The whole system is then maintained at a temperature between 50° and 60° C. in an oven, for 10 to 20 hours. During this time, the polymerization of the monomeric mixture takes place in 42.

The monomeric mixture is essentially an aqueous solution of HEMA or its mixture with hydrophobic monomers, of 70 to 95% by weight concentration in water. To this solution, a crosslinking agent (0.2 to 1% by weight based on the total amount of monomers), and a water-soluble initiator (0.05 to 1% by weight based on the total amount of monomers) are added. It is to be emphasized as a part of this invention that only hydrophobic monomers are used in conjunction with HEMA for the production of the central transparent hydrogel, since the resulting material must have a strength sufficient to prevent tearing or cutting by the sutures. The hydrophobic monomers have usually a strengthening effect upon hydrogels. It is also to be emphasized as a part of this invention that the concentration of water in the monomeric mixture should not exceed 30% by weight, since the resulting hydrogel must be transparent. Higher concentration of water may induce phase separation with loss of transparency, especially when hydrophobic comonomers are present in formulation.

Representative of other monomers useful in conjunction with HEMA as comonomers for the production of the prosthetic central portion of the present invention are the hydrophobic aliphatic methacrylates and acrylates, such as methyl methacrylate or cyclohexyl methacrylate, and 2-alkoxyethyl methacrylates and acrylates. These comonomers may be added to HEMA in any proportion from 1 to 20% by weight based on the total amount of monomers. When the amounts of the comonomers used are high, the amount of water in the mixture is reduced accordingly so that no phase separation would occur prior to or during polymerization.

As crosslinking agents and initiators, those aforementioned as usable for the manufacture of the prosthetic rim, may also be used unrestrictedly for the manufacture of the prosthetic central portion in the same proportions.

In a preferred formulation for the production of the prosthetic central hydrogel of the invention, 3.4 g HEMA are mixed with 0.6 g 2-ethoxyethyl methacrylate, as a comonomer, and 0.02 g ethylene dimethacrylate, as a crosslinking agent. To this mixture, 0.8 g distilled water are added and the resulting solution (80% by weight monomers in water) is thoroughly homogenized by stirring or shaking. Following this, 200 microliters of a solution 1% by weight 2,2'-azobis(N,N'-dimethyleneisobutyramidine)dihydrochloride in water are added as an initiator. The mixture is homogenized and deaerated for 5 minutes in an ultrasonic bath, and then slowly added into the enclosure 42. The polymerization then proceeds as aforedescribed, at 50° C. for 17 hours.

At the end of the second stage of the manufacturing process, the mould 40 is opened and the resulting device is removed and placed in distilled water for washing to a steady state with respect to extractables and for swelling to an equilibrium. The device is stored in water for at least one week, with daily water exchanges. The device, which is purposely larger in size than normally envisaged for a keratoprosthesis and needs therefore to be adjusted, is then frozen at −70° C., and cut to the required size and curvature in a diamond-tool lathing machine. During lathe processing, dry ice is placed on a sieve within a stainless steel funnel above the cutting tool in order to provide a continuous stream of cold carbon dioxide vapours for cooling purposes. The adjusted device is then washed abundantly in distilled water, and sterilized preferably by autoclaving at 120° C. for 20 minutes. The device is stored in sterile phosphate buffer saline until implantation.

The keratoprosthesis of the invention may be used as such, or it may be impregnated with collagen before implantation in order to increase the rate of cellular invasion. To perform this, the sterilized device is stirred for 24 hours in a cold (4° C.), neutral (pH 7.4) aqueous solution of sterile collagen with a concentration of 1.35 mg collagen per 1 milliliter solution. The solution containing the device is then warmed to 37° C. and incubated for 1 hour. The device is transferred into sterile phosphate buffer saline, where it is stored until implantation.

In the composite keratoprosthesis of the invention, the hydrogel sponge and the central hydrogel are permanently joined along the circular borderline zone between the rim and the central portion. This tight attachment is achieved by the penetration, prior to polymerization in the second stage, of the monomer solution into the pores of the pre-existent sponge. Over a certain distance in the sponge the transparent hydrogel is thus polymerized on the matrix of the sponge. A sequential interpenetrating polymer network (IPN) is also formed by the penetration of the monomers through diffusion in the substance of the sponge, in other words through swelling.

Various other embodiments will become evident to those skilled in the art. For example, by using a slightly modified moulding unit, the spongy rim may be produced in the second stage, after the central portion was made.

The surgical method which is employed for implantation of the keratoprosthesis of the invention is not particularly complicated, yet it is to be carefully performed, under a microscope and using suitable surgical tools, known to those skilled in the art.

Figure 5:
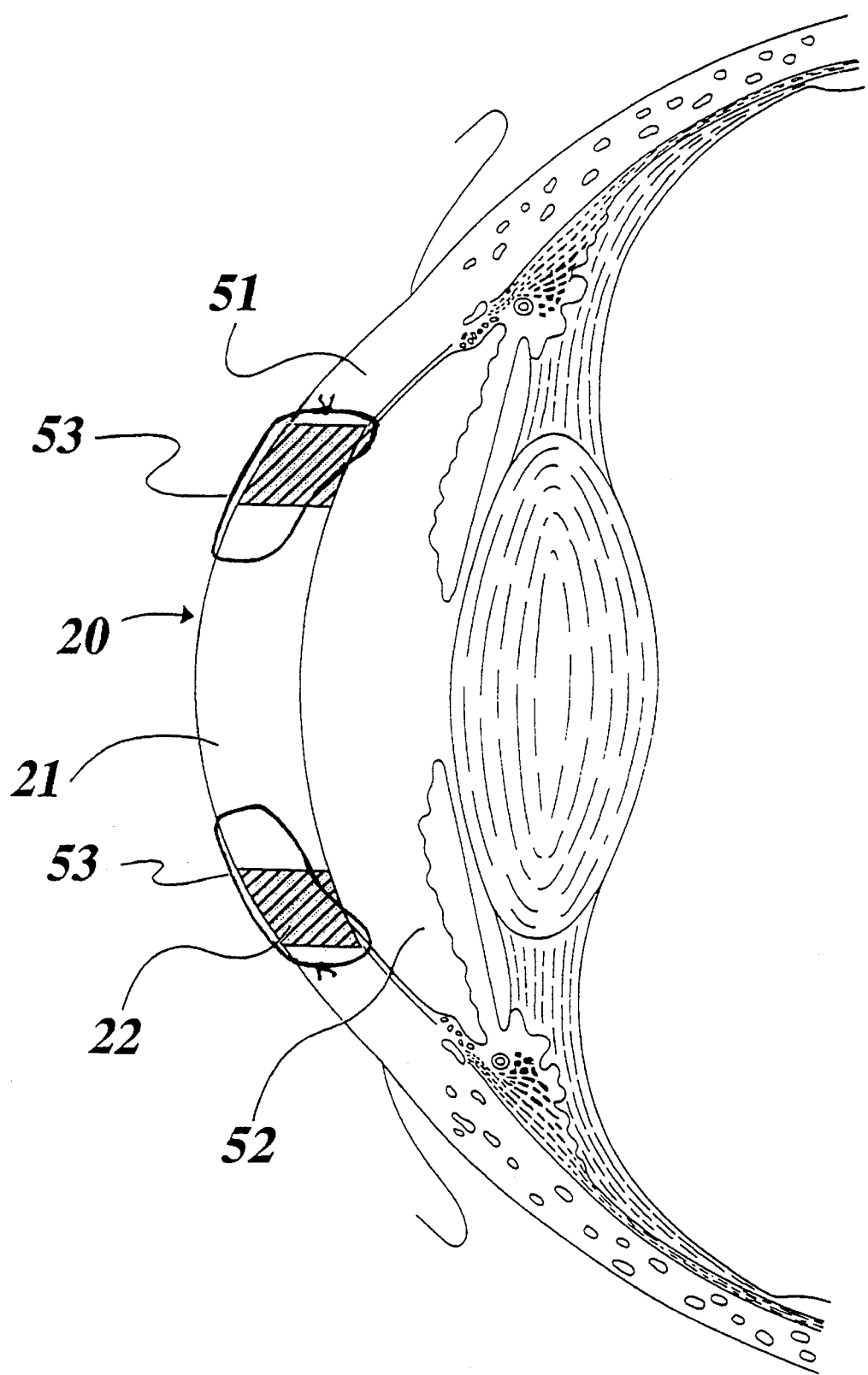
FIG. 5 is a cross-sectional view of the anterior segment of the human eye showing a keratoprosthesis of the invention implanted.

The keratoprosthesis is implanted in the eye as follows, with reference to FIG. 5. A full thickness circular trephination is performed in the centre of the recipient cornea 51, and the removal of the corneal button is completed in the usual manner using either scissors or a knife. The diameter of the corneal button to be removed is precisely determined so that a sufficient amount of host tissue is left to enable the keratoprosthesis of the invention to be implanted. Preferably, the device should be manufactured shortly prior to implantation so that the correct sizing to the individual patient may be accomplished. The recipient bed is purposely made 0.75 mm smaller than the real diameter of the keratoprosthesis in order to provide a mechanically tight fit when inserted.

A viscoelastic material, such as Healon®, is then injected into the anterior chamber 52 to maintain its shape for ease of insertion of the keratoprosthesis. Twelve to sixteen interrupted non-absorbable monofilament sutures 53 (nylon or prolene) of size 9/0 or 10/0 are then inserted through the transparent portion of the keratoprosthesis. They are placed 0.5 mm centrally to the junction between the spongy rim 22 and transparent portion 21 and passed to approximately three quarters of the thickness of the transparent portion, and then passed into the spongy rim and allowed to exit through the inferior aspect of the said rim. The suture pass is then completed through the recipient corneal tissue 51, tied on this side, and the knot buried within the host cornea. It is important to hold the keratoprosthesis with a specially designed broad non-toothed forceps which predominantly hold the central portion 21 and do not compress the spongy rim 22. Initially, four cardinal sutures are inserted and the remaining sutures evenly spaced as in routine corneal transplant surgery. The viscoelastic material is left inside the anterior chamber 52 to prevent initial leakage through the spongy rim 22 while cellular invasion occurs. In the initial post operative stages, it may be necessary to cover the whole keratoprosthesis with a thin conjunctival flap provided that sufficient conjunctiva is available. This may be removed later, after cellular adhesion has occurred.

While an advantageous and preferred embodiment of the present invention has been selected and described as an illustration of the invention, it should be understood by those skilled in the art that changes and adaptations can be made therein without departing from the scope of the invention as defined in the appended claims.

What is claimed is:

1. A method for the production of a keratoprosthesis comprising a central transparent portion which is a hydrogel composed essentially of a biocompatible hydrophilic polymer and a peripheral portion composed of a porous material which is a hydrogel sponge composed essentially of a biocompatible hydrophilic polymer, said central portion and said peripheral portion being intimately attached; wherein the peripheral portion is first formed by polymerization of the appropriate monomer or monomer mixture; the central portion being subsequently formed by polymerization of the appropriate monomer or monomer mixture while at least partially in contact with the already formed peripheral portion; and both the central and peripheral portions are formed in the same molding unit.

2. A method as claimed in claim 1, wherein the central portion is formed by polymerization of 2-hydroxyethyl methacrylate monomer in water.

3. A method as claimed in claim 2, wherein the concentration of 2-hydroxyethyl methacrylate monomer in water is about 70 to about 95% by weight.

4. A method as claimed in claim 1, wherein the central portion is obtained by the polymerization of 2-hydroxyethyl methacrylate monomer and a hydrophobic monomer in water.

5. A method as claimed in claim 4, wherein the total concentration of monomers in water is about 70 to about 95% by weight.

6. A method as claimed in claim 1, wherein the polymerization is carried out a temperature in the range of about 50° to about 60° C.

7. A method as claimed in claim 1, wherein the polymerization is carried out for a period of about 10 to about 20 hours.

8. A method as claimed in claim 1, wherein the peripheral portion is formed by the polymerization of 2-hydroxyethyl methacrylate monomer in water, optionally in the presence of a further monomer which is a hydrophilic monomer or a hydrophobic monomer.

9. A method as claimed in claim 8, wherein the total concentration of monomer in water is about 5 to about 25% by weight.

10. A method as claimed in claim 9, wherein the polymerization is carried out a temperature in the range of about 50° to about 80° C.

11. A method as claimed in claim 8, wherein the polymerization is carried out for a period of about 5 to about 10 hours.

12. A method as claimed in claim 1, wherein the polymerizations are carried out in the presence of a crosslinking agent and an initiator.

13. A method as claimed in claim 12, wherein the crosslinking agent is selected from polyfunctional methacrylates, polyfunctional acrylates, bis(acrylamide) and divinyl derivatives.

14. A method as claimed in claim 12, wherein the amount of crosslinking agent is about 0.2 to about 1% by weight of the total amount of monomers.

15. A method as claimed in claim 12 wherein the initiator is selected from aqueous solutions of sodium metabisulfite and ammonium persulphate, 2-2'-azobis(N,N'-dimethyleneisobutyramidine)dihydrochloride and 2,2'-azobis(2-amidinopropane)dihydrochloride.

16. A method as claimed in claim 15, wherein the amount of initiator is about 0.05 to about 1% by weight of the total amount of monomers.

17. A method as claimed in claim 1, wherein the central portion is formed first and the peripheral portion is formed by polymerizing the appropriate monomer mixture in a space at least partially bounded by the central portion.

18. A method as claimed in claim 1, wherein the peripheral portion is formed first and the central portion is formed by polymerizing the appropriate monomer mixture in a space at least partially bonded by the peripheral portion.

19. A process for the production of a keratoprosthesis comprising the steps of:
   (a) assembling a moulding unit comprising a head member and a base member, said head member and said base member being arranged to at least partially define a first space;
   (b) introducing a first monomeric mixture comprising either:
      (A) 2-hydroxyethyl methacrylate monomer and optionally a further monomer which is a hydrophilic monomer or a hydrophobic monomer; or
      (B) 2-hydroxyethyl methacrylate monomer and optionally a hydrophobic monomer into said first space;
   (c) inserting a first plunger means into said first space such that said first mixture is substantially contained within a first moulding space at least partially bounded by a surface of said first plunger means and a surface of said base member;
   (d) causing or allowing polymerization of said first monomeric mixture to occur;
   (e) extracting said first plunger means from said first space;
   (f) introducing a second monomeric mixture comprising the other of (A) or (B) defined in step (b) above into a second moulding space at least partially bounded by a surface of the polymerized first monomeric mixture and a surface of said base member; and
   (g) causing or allowing polymerization of said second monomeric mixture to occur so as to thereby form the keratoprosthesis.

20. A process as claimed in claim 19 wherein said first plunger means has a bore extending therethrough and excess first monomeric mixture not contained in said first moulding space can be extracted after step (c) through said bore in said first plunger means.

21. A process as claimed in claim 19 further comprising the step of introducing a second plunger means having a bore extending therethrough into said second moulding space and extracting any excess of said second monomeric mixture in said second moulding space through said bore in said second plunger means.

22. A process as claimed in claim 19 wherein said first plunger means is inserted into said first space bypassing said first plunger means through an aperture in said head member.

23. A process as claimed in claim 19 wherein the moulding unit is maintained at a temperature in the range of about 50° to about 80° C. for a period of about 5 to about 10 hours during either step (d) or step (g) when said first or second monomeric mixture comprises (A).

24. A process as claimed in claim 19, wherein the moulding unit is maintained at a temperature in the range of about 50° to about 60° C. for a period of about 10 to about 20 hours during either step (d) or step (g) when said first or second monomeric mixture comprises (B).

25. A process as claimed in claim 19, wherein after step (g) the keratoprosthesis is frozen at about −70° C. and then shaped to the required size and curvature.

26. A process as claimed in claim 25, wherein the keratoprosthesis is subsequently shaped using a diamond-tool lathe.

27. A process as claimed in claim 19, wherein the keratoprosthesis is maintained in a sterile solution until implantation.

28. A process as claimed in claim 19, wherein the keratoprosthesis is impregnated with collagen prior to implantation in order to increase the rate of cellular invasion.

* * * * *

UNITED STATES PATENT AND TRADEMARK OFFICE
CERTIFICATE OF CORRECTION

PATENT NO. : 5,458,819

DATED : October 17, 1995

INVENTOR(S) : CHIRILA et al.

It is certified that error appears in the above-indentified patent and that said Letters Patent is hereby corrected as shown below:

Column 2, line 36, delete "interlace" and insert therefor --interface--.

Claim 6, column 9, line 56, immediately following "out" insert --at--.

Claim 10, column 10, line 3, immediately following "out" insert --at--.

Cancel claim 17 at column 10, lines 26 through 29.

Claim 22, column 11, line 10, delete "bypassing" and insert therefor --by passing--

Signed and Sealed this

Seventeenth Day of September, 1996

Attest:

BRUCE LEHMAN

Attesting Officer     Commissioner of Patents and Trademarks